US00PP10010P

United States Patent [19]

Davis

[11] Patent Number: Plant 10,010

[45] Date of Patent: Aug. 26, 1997

[54] APPLE TREE NAMED 'DAVIS'

[76] Inventor: Nick L. Davis, 609 American Fruit Rd., Wenatchee, Wash. 98801

[21] Appl. No.: 628,457

[22] Filed: Apr. 5, 1996

[51] Int. Cl.[6] ..... A01H 5/00

[52] U.S. Cl. ..... Plt./34.1

[58] Field of Search ..... Plt./34.1

*Primary Examiner*—James R. Feyrer

*Attorney, Agent, or Firm*—Klarquist Sparkman Campbell Leigh & Whinston LLP

[57] ABSTRACT

A new and distinct variety of apple tree (*Malus pumila*) named 'Davis' characterized by its distinct ripening season, between that of Red Delicious and Braeburn, its distinct cherry red, striped pattern over 50 to 100 percent of the fruit surface, prominent white lenticels, and a creamy white flesh color.

3 Drawing Sheets

BACKGROUND OF THE INVENTION

The present invention comprises a new and distinct variety of apple tree (*Malus pumila*), referred to by the varietal name 'Davis.'

The parent tree of the new variety was a sucker that emerged from seedling rootstock of Red Delicious cv. 'Bisbee' (U.S. Plant Pat. No. 1,565) in my orchard on American Fruit Road, Wenatchee, Chelan County, Wash. The sucker was not removed from the Red Delicious rootstock. It was observed that fruit formed on the sucker was distinct from Red Delicious, having characteristics of shape and appearance most closely resembling the Gala variety, but distinct from Gala, Royal Gala, known Gala sports, or other known apple varieties in shape, size, color pattern, and flesh characteristics, for example. Second and third generation trees of the new variety have been grafted to other Red Delicious trees on my property.

This invention has not been observed under all possible environmental conditions. However, the following combination of traits have been repeatedly observed in asexually propagated progeny and are determined to be the basic characteristics of this invention, which in combination distinguish this variety from the Gala variety as a new and distinct variety of apple: (1) smaller leaf weight; (2) shorter petiole length; (3) shorter leaf blade; (4) lower ratio of leaf length to width; (5) lower ratio of fruit length to width; (6) rounder fruit (as compared with Gala's distinctive round-conic shape); (7) a distinct cherry red, striped pattern over 50 to 100 percent of the fruit surface; (8) fruit having a distinctly whiter ground color and flesh color (as compared to Gala's yellowish flesh); (9) absence of lobes at the apex (calyx end) of most fruits (as compared to Gala's moderately lobed fruit); (10) distinctly shallower basin of fruit; (11) prominent white lenticels; and (12) a ripening season between that of red Delicious and Braeburn, with fruit harvested approximately 30 days later than Gala.

Table 1 shows the primary differences in leaf and fruit characteristics between 'Davis' and Gala (Royal Gala cv. 'Tenroy,' U.S. Plant Pat. No 4,121):

TABLE 1

| | Davis | Royal Gala | % Diff. from Gala |
|---|---|---|---|
| Leaf wt. (g)* | 0.80 | 1.04 | −23.1 |
| Petiole length (mm)* | 27.0 | 29.0 | −6.9 |
| Leaf blade length (mm)* | 85.4 | 98.9 | −3.5 |
| Leaf blade width (mm)* | 55.1 | 56.4 | |

TABLE 1-continued

| | Davis | Royal Gala | % Diff. from Gala |
|---|---|---|---|
| Leaf blade length/width ratio | 1.55 | 1.75 | −11.4 |
| Fruit length (mm)** | 65.6 | 68.8 | |
| Fruit diameter (mm)** | 73.5 | 75.5 | |
| Fruit length/diameter ratio | 0.878 | 0.910 | −3.5 |
| Shape of fruit | Round oblate | Round conic | |
| Skin ground color | Cream | Yellow | |
| Flesh color | Cream | Yellow | |
| Calyx lobes | Absent | Present | |
| Basin depth (mm) | Shallow (+/− 5 mm) | Medium (+/− 8 mm) | |
| Basin width (mm) | 30.0 | 28.0 | |
| Average harvest date | 10/08 | 09/08 | |

*Average of 50 leaves
**Average of 50 fruit

The foregoing characteristics and differences are stable and have been observed since first discovery. Davis cannot be confused with any other cultivar now in commerce in the U.S.

The new variety is readily identified by the uniformity of these characteristics. To the inventor's knowledge, this combination of characteristics distinguishes this new variety from all varieties of Gala apple or other apple varieties of which I am aware.

Asexual reproduction through two generations on several trees shows that these characteristics are established and transmitted through succeeding asexual propagations.

DETAILED DESCRIPTION

Figure 1:
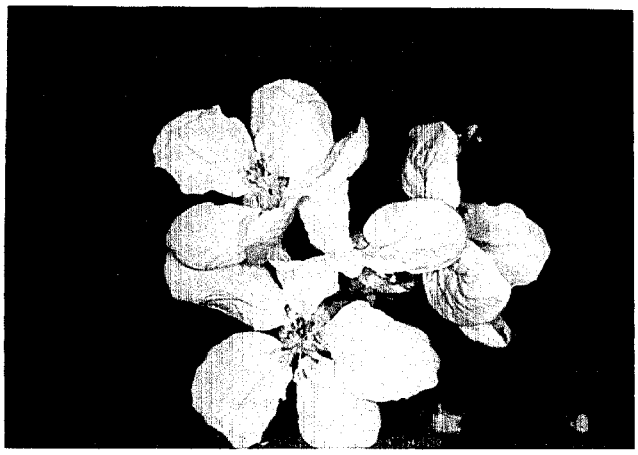
FIG. 1 is a view of a flower cluster of Davis taken April 1994.
Figure 2:
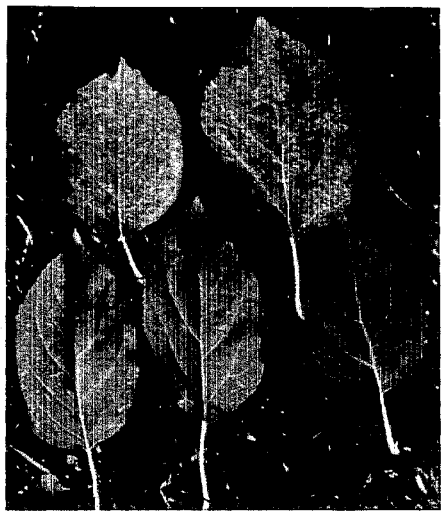
FIGS. 2, 3 are views of typical leaves of Davis (FIG. 2) and Gala (FIG. 3) taken October 1993 showing the characteristic rounder shape of leaves of Davis.
Figure 3:
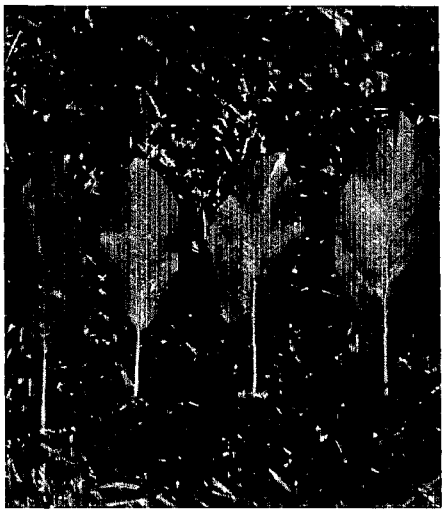
Figure 4:
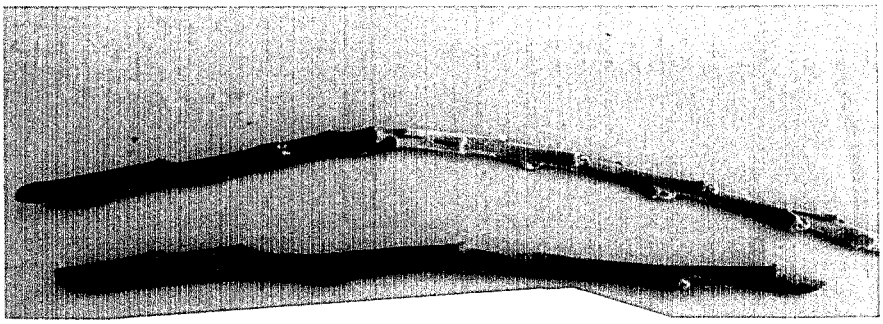
FIG. 4 is a view of typical one-year shoots of Davis taken on Oct. 3, 1995.
Figure 5:
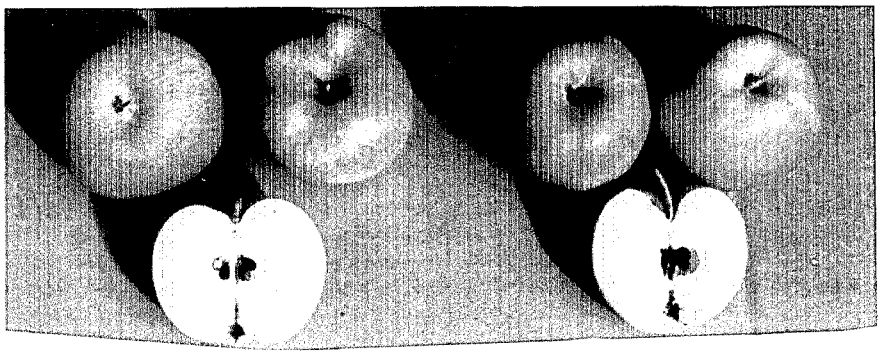
FIG. 5 is a view of fruit of Davis (left) and Royal Gala (right grown in the same block at my orchard in Wenatchee, Wash., and taken on Oct. 13, 1995, showing differences in fruit shape, skin coloring, lenticels, and flesh color.
Figure 6:
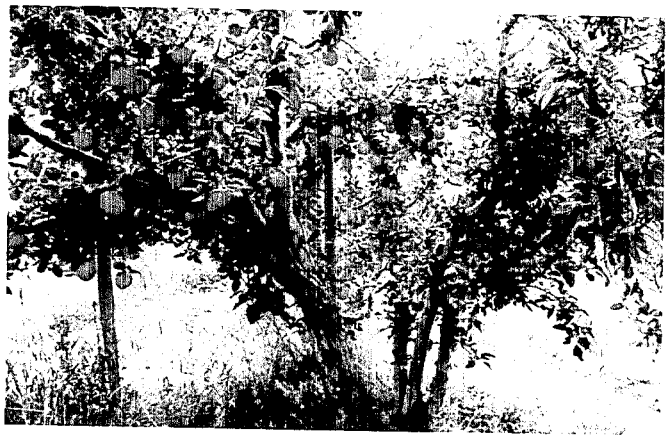
FIG. 6 is a view of an original tree of Davis, showing the original Red Delicious trunk and the "sucker" shoot of Davis.
Figure 7:
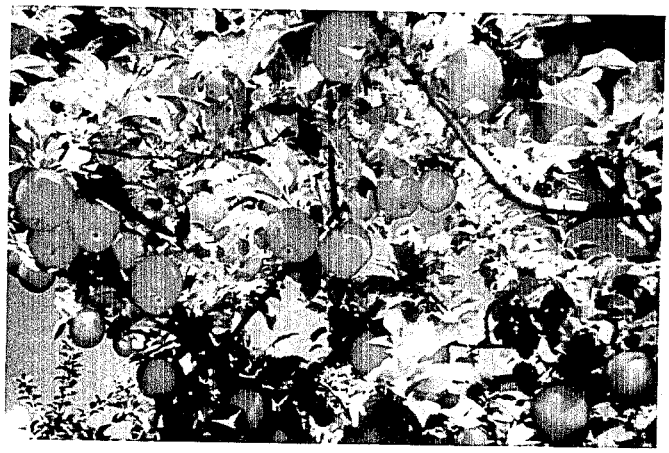
FIG. 7 is a view of fruit on a Davis tree taken on Oct. 8, 1994.

The following is a detailed description of the invention based on plants produced under commercial practices in my orchard in Wenatchee, Wash and observed at this location. All trees were of eating ripe maturity, which, in the case of the new variety, is also harvest maturity.

Color references are made in accordance with Ridgeway, R., Color Standards and Color Nomenclature, Washington, D.C., 1912, except where general color terms of ordinary dictionary significance is obvious.

All trees of the new variety, insofar as I have been able to observe them, have been identical in all the characteristics described below. Other than as set forth below, as of this time I have not observed any other characteristics which are different from seedling Gala apple trees.

Propagation: Holds to distinguishing characteristics through succeeding propagation by rooted cuttings.

Parentage: Seedling rootstock of a Red Delicious apple tree, i.e., suckers which arose from the rootstock of this cultivar and were allowed to fruit.

Locality where grown and observed: Nick Davis Orchard, American fruit Road, Wenatchee, Wash.

Date of fruit maturity: Approximately Oct. 15, 7 days after Red Deliciuos, 30 days after Gala, approximately with Rome Beauty, and slightly before Braeburn.

Tree: Medium vigor, upright spreading, hardy, productive, annual bearing, primarily on spurs.

Trunk: Stocky, light brown to reddish brown.

Branches: Spreading, freely branching, one-year shoots, more slender than those of Gala, medium-brown to grayish in color, cream to tan colored, round, medium in density.

Internodes: Average internode length 24 mm (compared to Gala's 28 mm).

Leaves (primary):

*Length.*—72 to 120 mm; average 85.4 mm. *Width.*—39 to 80 mm; average 55.1 mm. *Petiole.*—27 mm average. *Margin.*—Finely serrate. *Tip.*—Medium-pointed. *Stipules.*—Medium size (5 to 17 mm in length), sharply pointed, borne in pairs.

*Color.*—Dark green, glossy on upper surface, lightly pubescent on lower surface; #21–14 (upper), #21–11 (lower Munsell Limited Color Cascade.

Leaves (secondary): Oval, dark green, glossy upper surface; lightly pubescent lower surface, identical in stipules and color to primary leaves, but smaller in size.

Flowers:

*Time of bloom.*—Mid-season (with Red Delicious).

*Size.*—Medium-large, petals touching.

*Color.*—Light pink, becoming white.

*Stamen.*—Single row, anthers bright yellow becoming yellowish brown.

*Pistil.*—Stigmas shorter than stamens.

*Sepals.*—Medium size, pubescent, convergent.

*Pollination requirements.*—Presumably satisfied by other diploid strains and crabapples.

Fruit:

*Maturity when described.*—Ripe when starch content is 4.0 to 5.0, harvested Oct. 8, 1995.

*Size.*—Medium-large (74–84 mm), one box size larger than Gala.

*Form.*—Round to round-oblate.

*Cavity.*—Round, medium depth, apex acute; breadth 35 mm; depth 15 mm.

*Basin (calyx).*—Medium size (32 mm), obtuse, very shallow, smooth (non-lobed), 5–8 mm; calyx closed, sepals short, touching; finely pubescent.

*Stem.*—Medium length and moderately thick—22 mm×3.0 mm (compared to Gala's 27 mm×2.0 mm).

*Skin.*—Smooth, without bloom, without greasiness; no tendency toward cracking or russeting; skin medium thick, medium toughness.

*Lenticels.*—Conspicuous, more numerous than on Gala, whitish in color.

*Ground color.*—Whitish yellow (Plate XVI, 21'. O-YY Massicot Yellow).

*Overcolor.*—Purplish red (Plate XII, 71. V-RR Pomegranate Purple) with dark red stripes (Plate XII, 71. V-RR Bordeaux) more prominent toward shoulder of exposed fruits.

*Average coloration.*—60% (range from 10 to 100%).

flesh: Cream (Plate XXX, 23". Yellow, Marguerite Yellow), becoming pale yellow with advanced maturity; crisp, juicy; no tendency to water core.

*Texture.*—Dense, somewhat woody, less melting than Gala.

*Flavor.*—Good, apple-like, distinctive (not similar to Gala).

*Aroma.*—Pronounced, apple-like fragrance.

Core: Longitudinal section broadly ovate, symmetrical; cross section round, medium size, seed cells closed.

Seed: Normally 10 to 16 total, 2.6 per cell, medium size, brown, length 8 mm, width 5 mm, oval in shape.

Storage: Up to 6 months in CA, 3 months in regular storage at 32° F (0° C).

Usage: Fresh, dessert.

I claim:

1. A new and distinct variety of apple tree substantially as herein shown and described.

* * * * *